(12) United States Patent
Sacks et al.

(10) Patent No.: US 6,706,534 B2
(45) Date of Patent: Mar. 16, 2004

(54) PULSED CARRIER GAS FLOW MODULATION FOR SELECTIVITY ENHANCEMENTS WITH GAS CHROMATOGRAPHY USING SERIES-COUPLED ENSEMBLES

(75) Inventors: Richard Douglas Sacks, Ann Arbor, MI (US); Tincuta Maria Veriotti, St. Joseph, MI (US); Megan Ellen McGuigan, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/016,798

(22) Filed: Dec. 10, 2001

(65) Prior Publication Data

US 2003/0109054 A1 Jun. 12, 2003

(51) Int. Cl.⁷ .............................................. G01N 30/32
(52) U.S. Cl. ..................... 436/161; 422/89; 73/23.36; 73/23.42; 95/86; 96/102; 96/103; 96/104
(58) Field of Search .................... 422/89; 436/161; 73/23.35, 23.36, 23.37, 23.42; 95/82, 86; 96/101, 102, 103, 104, 106

(56) References Cited

U.S. PATENT DOCUMENTS

| | | |
|---|---|---|
| 4,925,306 A | 5/1990 | Sacks et al. |
| 5,096,471 A | 3/1992 | Sacks et al. |
| 5,141,532 A | 8/1992 | Sacks et al. |
| 5,141,534 A | 8/1992 | Sacks et al. |
| 5,205,845 A | 4/1993 | Sacks et al. |
| 5,281,256 A | 1/1994 | Sacks et al. |
| 5,288,310 A | 2/1994 | Peters et al. |

OTHER PUBLICATIONS

Instrumental Methods of Analysis, Sixth Edition, Willard et al, eds., Wadsworth Publishing Company, Belmont, Ca (1981) pp. 465 and 570.*
Leonard et al., Anal. Chem. (1999), vol. 71, pp. 5501–5507.*
Tincuta Veriotti, Megan McGuigan, and Richard Sacks, "Pulsed Flow Modulation for High–Speed GC Using a Pressure–Tunable Column Emsemble", Analytical Chemistry 2001, vol. 73, No. 2, Jan. 15, 2001, pp. 279–285, Published on Web Dec. 14, 2000.
Tincuta Veriotti and Richard Sacks, "A Tandem Column Ensemble with an Atmospheric Pressure Junction–Point Vent for High–Speed GC with Selective Control of Peak–Pair Separation", Analytical Chemistry 2001, vol. 73, No. 4, Feb. 15, 2001, pp. 813–919, Published on Web Jan 23, 2001.
Tincuta Veriotti and Richard Sacks, "High–Speed GC and GC/MS with a Series–Coupled Column Ensemble Using Stop–Flow Operation", Analytical Chemistry 2001, vol. 73, No. 13, Jul. 1, 2001, pp. 3045–3050, Published on Web May 17, 2001.

(List continued on next page.)

*Primary Examiner*—Jan Ludlow
(74) *Attorney, Agent, or Firm*—Harness, Dickey & Pierce, P.L.C.

(57) ABSTRACT

A gas chromatography system having a computer-controlled pressure controller that delivers pressurized pulses to a column junction point of two series-coupled columns having different stationary-phase chemistries and a method of using the same. Each pressurized pulse causes a differential change in the carrier gas velocities in the two columns, which lasts for the duration of the pressurized pulse. Whereby, the pressurized pulse selectively increases the separation of a component pair that exhibits separation at the exit of the first column, but otherwise co-elutes from the column ensemble.

18 Claims, 8 Drawing Sheets

OTHER PUBLICATIONS

Tincuta Veriotti and Richard Sacks, "High–Speed GC and GC/Time–of–Flight MS of Lemon and Lime Oil Samples", Analytical Chemistry 2001, vol. 73, No. 18, Sep. 15, 2001, pp. 4395–4402, Published on Web Aug. 10, 2001.

Joshua Whiting and Richard Sacks, "Selectivity Enhancement for High–Speed GC Analysis of Volatile Organic Compounds with Portable Instruments Designed for Vacuum–Outlet and Atmospheric–Pressure Inlet Operation Using Air as the Carrier Gas", Analytical Chemistry 2002, vol. 74, No. 1, Jan. 1, 2002, pp. 246–252.

* cited by examiner

PULSED CARRIER GAS FLOW MODULATION FOR SELECTIVITY ENHANCEMENTS WITH GAS CHROMATOGRAPHY USING SERIES-COUPLED ENSEMBLES

FIELD OF THE INVENTION

The present invention relates to chemical mixture analysis and, more particularly, relates to a practical approach for achieving improved selectivity for capillary gas chromatography using pulsed carrier gas flow modulation.

BACKGROUND OF THE INVENTION

Gas chromatography is an analytical technique for separating compounds from a mixture based on their volatilities and polarities. Gas chromatography thus provides both qualitative and quantitative information for the individual compounds present in a sample. These compounds move through a gas chromatography column as gases, either because the compounds are normally gases or because they have been heated and vaporized into a gaseous state. The compounds partition between a stationary phase, which can be either solid or liquid, and a mobile phase, which is typically gas.

As is known in the art, the introduction of the fused silica, wall-coated, capillary gas chromatography column in 1979 represented a paradigm shift in the analysis of volatile and semi-volatile organic compounds. However, with the introduction of the fused-silica capillary column, the emphasis gradually shifted towards the development of more universal columns with greater resolving power for a wider variety of compound mixtures.

Long capillary columns (generally greater than 20 m long) generally provide greater resolving power and, thus, the complete separation of more complex mixtures with analysis times comparable to those achieved with packed columns.

Briefly, as used herein, "selectivity" generally refers to the pattern of peaks produced from the gas chromatography column and the values of the retention factor ratios for all component pairs. Retention factor is equal to the difference between the retention time and the column void time ratioed to the void time. The greater the selectivity of the column for a specified component pair, the more separation between the corresponding peaks of the chromatogram can be achieved.

On the other hand, shorter capillary columns (generally 5–20 m long), which are operated at relatively high carrier gas flow rates, have been used to obtain faster mixture separations. However, in exchange for faster mixture separations, resolving power is sacrificed. As should be appreciated, if these techniques for high-speed gas chromatography are to be useful for more complex mixtures, selectivity or resolving power must be improved.

Accordingly, there exists a need in the relevant art to provide a method and apparatus whereby a wide variety of compounds may be quickly separated into component parts without significantly affecting the resolving power. Furthermore, there exists a need in the relevant art to provide a method and apparatus of capillary column gas chromatography that is capable of varying the selectivity during the course of the compound analysis to provide improved selectivity capability of various specific compound pairs. Still further, there exists a need in the relevant art to provide a method and apparatus of pulsed carrier gas flow modulation for improved selectivity of gas chromatography. Additionally, there exists a need in the relevant art to provide a method of capillary gas chromatography that overcomes the disadvantages of the prior art.

SUMMARY OF THE INVENTION

According to the principles of the present invention, a gas chromatography system is provided having an advantageous construction and method of using the same. The gas chromatography system includes a computer-controlled pressure controller that delivers pressurized pulses to a column junction point of two series-coupled columns having different stationary-phase chemistries. Each pressurized pulse causes a differential change in the carrier gas velocities in the two columns, which lasts for the duration of the pressurized pulse. Whereby, the pressurized pulse selectively increases the separation of a component pair that exhibits separation at the exit of the first column, but otherwise co-elutes from the column ensemble.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2(*b*) is a graph illustrating application of a pressurized pulse to the pair of illustrative components after one of the components has reached the column junction point;

FIG. 2(*c*) is a graph illustrating application of a pressurized pulse to the pair of illustrative components after both components have reached the column junction point;

FIG. 2(*d*) is an enlarged graph and chromatogram of box 1(*d*) of FIG. 1(*a*);

FIG. 2(*e*) is an enlarged graph and chromatogram of box 1(*e*) of FIG. 1(*b*);

FIG. 2(*f*) is an enlarged graph and chromatogram of box 1(*f*) of FIG. 1(*c*);

DETAILED DESCRIPTION OF THE PREFERRED EMBODIMENTS

The following description of the preferred embodiment is merely exemplary in nature and is in no way intended to limit the invention, its application, or uses.

As will be described in detail herein, the present invention provides a method and apparatus for achieving improved selectivity for gas chromatography with capillary columns. The present invention comprises a computer-controlled pressure controller that delivers pressurized pulses to a column junction point of two series-coupled columns having different stationary-phase chemistries. Each pressurized pulse causes a differential change in the carrier gas velocities in the two columns, which lasts for the duration of the pressurized pulse. The pressurized pulse selectively increases the separation of a component pair that exhibits separation at the exit of the first column, but otherwise co-elutes from the column ensemble. If both components are on the same column when the pressurized pulse is applied, the component separation remains essentially unchanged despite an overall shift in retention times. If one component of the pair is on the first column and the other component is on the second column, a pressurized pulse can result in a large change in the ensemble separation for the component pair, thereby increasing the peak separation in the chromatogram to aid in quantitation and identification.

A significant limitation of known prior art methods is the fact that a change in the pressure at the column junction point used to increase the separation of a particular component pair often results in reduced separation of one or more other component pairs. Thus, the selection of a pressure at the column junction point for a specified set of target compounds previously required a compromise. However, the present invention preferably employs a relatively short pressurized pulse to increase the separation of a specific component pair without significantly affecting the peak pattern and separation of the remaining components in the mixture.

Figure 1:
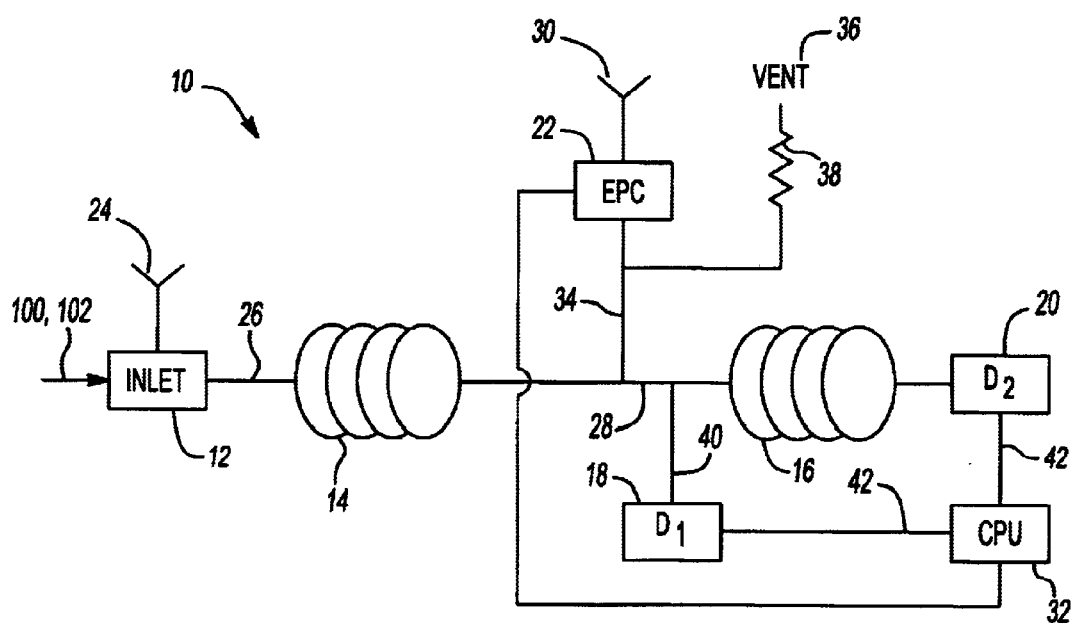
FIG. 1 is a schematic drawing illustrating a gas chromatography system according to the principles of the present invention.

Referring now to FIG. 1, a pressure-controlled, dual-column, gas chromatography system is schematically illustrated in accordance with a first embodiment of the present invention, generally indicated at 10. Gas chromatography system 10 generally includes an inlet system 12, a first gas chromatography separation capillary column 14, a second gas chromatography capillary column 16, a first detector ($D_1$) 18, a second detector ($D_2$) 20, and an electronic pressure controller 22.

Inlet system 12 is configured generally to receive a sample "plug" of an analyte mixture for analysis within gas chromatography system 10. More particularly, a stream of carrier gas from a carrier gas supply 24 entrains such analyte mixture during injection. This entrained analyte mixture and carrier gas composite is introduced into first column 14 through a passage 26. Various configurations of inlet system 12 can be provided, such as mechanical injection valves, cryofocusing systems, and the like.

Similarly, first column 14 and second column 16 may take various forms, including columns having various types of liquid stationary phase materials. In addition, solid stationary phase-type columns using adsorbent materials, such as what is commonly known as porous layer open tubular (PLOT) columns or liquid crystal columns. Columns having polar or non-polar stationary phases may be used. However, for discussion purposes in the present disclosure, it is preferred that first column 14 is an approximately 10 m long, 0.25 mm diameter (id) column having a 0.25-$\mu$m thick bonded, stationary-phase, trifluoropropylmethyl polysiloxane film, while second column 16 is an approximately 10 m long, 0.25 mm diameter (id) column having a 0.25-$\mu$m thick bonded, stationary-phase, dimethyl polysiloxane film.

First column 14 and second column 16 are coupled in series along a column junction point 28. Electronic pressure controller 22, which is capable of pressure step sizes of approximately 0.1 psi and pressure repeatability of ±0.01 psi, is fluidly coupled to column junction point 28. An adjustable pressure source carrier gas supply 30 is provided in fluid connection with electronic pressure controller 22 to apply pressurized pulses to column junction point 28 in accordance with the principles of the present invention. Preferably, electronic pressure controller 22 is driven in response to a central processing unit 32. Moreover, electronic pressure controller 22 is preferably coupled to column junction point 28 via an approximately 1.0 m long, 0.25 mm diameter (id) uncoated, fused-silica tube 34, which is further vented to atmosphere at 36. A restrictor member 38 may be used to restrict the bleed off of the pressurized pulse. Restrictor member 38 is used to reduce the pressure equilibration time for downward pressure changes and to prevent contamination of electronic pressure controller 22. Preferably, carrier gas supplies 24 and 30 each consists of purified hydrogen, helium, air, or other gases.

Adjustment of this carrier gas pressure via electronic pressure controller 22 results in a differential change in the carrier gas velocities between first column 14 and second column 16, which will result in output changes in the gas chromatogram. That is, an increase in the pressure at column junction point 28 results in reduced carrier gas velocity on first column 14, yet increased velocity on second column 16. If the void time of first column 14 increases and the void time of second column 16 decreases (due to an increase in the pressure at column junction point 28), the mixture components have increased residence time on first column 14 and decreased residence time on second column 16. Consequently, this arrangement increases the influence of the stationary-phase chemistry of first column 14 and decreases the influence of the stationary-phase chemistry of second column 16. Alternatively, a reduction in the pressure at column junction point 28 has the opposite effect.

First detector 18 is coupled to column junction point 28 to monitor a portion of the effluent from first column 14. Similarly, second detector 20 is coupled to the output of second column 16 to monitor the output from second column 16 and, thus, column ensemble 14, 16. Preferably, a 1.0 m long, 0.10 mm diameter (id), deactivated, fused-silica tube 40 is used to transport approximately 10% of the effluent from first column 14 to first detector 18. However, any size tube may be used, although shorter tubes provided generally improved results. As will be described below, a chromatogram is obtained from first detector 18 to determine the time at which to initiate the pressurized pulse from electronic pressure controller 22 to column junction point 28. Preferably, first and second detectors 18 and 20 are each two flame-ionization detectors. However, it should be appreciated that first detector 18 and second detector 20 may be any detector capable of providing sufficient results, such as but not limited to flame-ionization detectors, photo-ionization detectors, thermal-conductivity detectors, solid-state sensors, mass spectrometers, flame photometric detectors, flame thermionic detectors, electron capture detectors, pulse helium ionization detectors, and the like. First detector 18 and second detector 20 each output a resultant signal to central processing unit 32 via communication lines 42. It should be understood that once the pressurized pulse initiation times are determined for a given mixture, first detector 18 may be eliminated, as the initiation time will remain the same for that mixture.

In order to obtain accurate void time values and retention time values for first column 14, the gas transport time from column junction point 28 to first detector 18 along tube 40 is subtracted from the measured retention times outputted from first detector 18. This gas transport time is computed using standard equations for gas flow in capillary tubes. It is further important to note that the gas transport time varies with the pressure at column junction point 28. Retention factors for first column 14 are computed from these corrected retention time and void time values using central processing unit 32. Void time and retention time values for second column 16 are further obtained by central processing unit 32 by subtracting the corresponding values for first column 14 from the ensemble values obtained from second detector 20.

The retention factor values for individual columns as well as the column dimensions and pressures and the viscosity of the carrier gas at the column operating temperature are used as inputs to a band-trajectory model. This band-trajectory model uses spreadsheet calculations and takes into account the carrier gas flow velocity profile along the column axis, the change in retention for each mixture component as it crosses the junction from the first to second column 16, and programmed changes in the pressure at column junction point 28.

Finally, the pressure at column junction point 28 in the absence of the pressurized pulse, also referred to as the quiescent pressure, is further chosen to be equal to the pressure that would occur at column junction point 28 in the absences of any external connections to column junction point 28, also referred to as the natural pressure. This natural pressure results in an ensemble void time that is near the minimum value achievable with the dual-column ensemble.

Discussion of Results

In some cases, a pair of mixture components can co-elute from a tandem-column ensemble if 1) both components have very similar retention factor values on both columns, or 2) if one of the components has a larger retention factor on one of the columns and the other component has a larger retention factor on the other column. In the former case, adjustment of the pressure at column junction point 28 may not separate the two components. Therefore, it may be necessary to use a longer column ensemble, which should provide improved resolving power or an ensemble with greater selectivity for the specific component pair may provide the only solution. However, in the latter case, a change in the pressure at column junction point 28 often will result in adequate separation of the component pair. However as mentioned above, in conventional methods, a change in the pressure at column junction point 28 may result in the co-elution of other component pairs that are previously separated.

Figure 2:
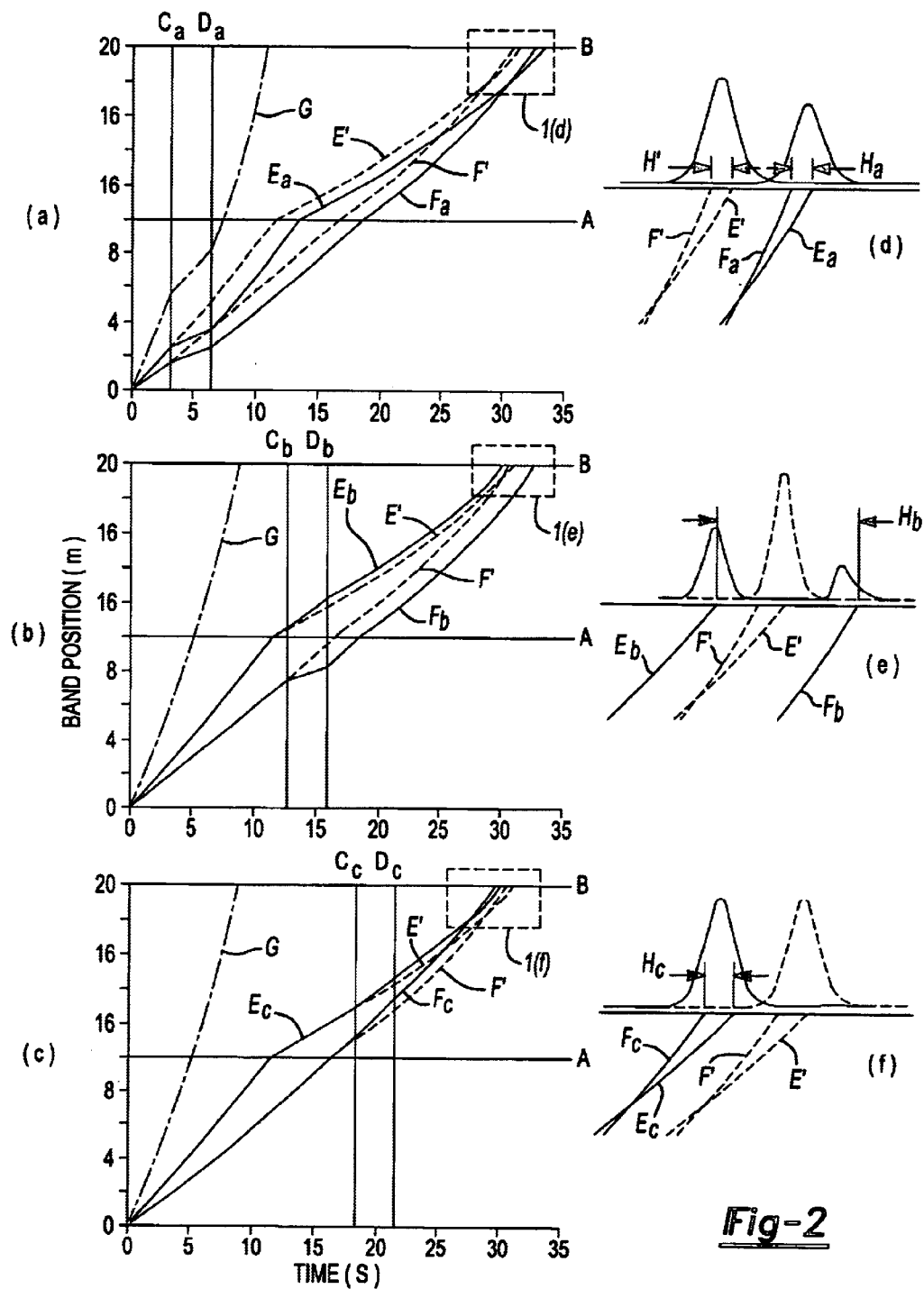
FIG. 2(*a*) is a graph illustrating application of a pressurized pulse to a pair of illustrative components prior to the components reaching a column junction point.

Referring now to FIGS. 2(a)–(c), according to the principles of the present invention the application of a pressurized pulse to column junction point 28 at an appropriate time after injection of the analyte mixture can be used to separate a specific and discrete component pair without significantly affecting the pattern of peaks for other mixture components. In particular, for each of the three cases illustrated in FIGS. 2(a)–(c), injection of the analyte mixture occurs at zero time in the lower left corner of the plots. A horizontal line A in the center of each figure corresponds to column junction point 28. Thus, the area below horizontal line A represent first column 14 and the area above horizontal line A represent second column 16. Therefore, elution from column ensemble 14, 16 occurs along the top horizontal line B at 20 m. A pair of vertical lines, generally indicated at C and D, in each of the three cases illustrates the time interval corresponding to the application of a 3-second wide (nominal) pressurized pulse from a quiescent value of 36.0 psia to 44.0 psia. It should be appreciated that the pressurized pulse may be of any duration necessary to facilitate separation of the component pair. A pair of band trajectories, generally indicated at E and F, represents a first component 100 and a second component 102 of the analyte mixture, respectively (see FIG. 1). For discussion purposes, first component 100 is n-octane and second component 102 is 1-pentanol. In each of FIGS. 2(a)–(c), solid lines, E and F, illustrate the case where a pressurized pulse is used, while the broken line illustrates the case where a pressurized pulse is not used for reference, generally indicated at E' and F'.

Still referring to FIGS. 2(a)–(c), a band trajectory G, represented by a line having alternate dots and dashes, illustrates the trajectory of an unretained component along the column-ensemble axis for the case with the pressurized pulse. As can been seen from FIGS. 2(a)–(c), this line for the unretained component illustrates no discontinuous slope change at column junction point 28. This condition exists because the natural pressure at column junction point 28 is used in the absence of a pulse.

As seen in FIGS. 2(d)–(f), an enlarged portion of FIGS. 2(a)–(c) is illustrated, respectively. More particularly, FIGS. 2(d)–(f) each illustrate the portion of the band trajectory plots in the broken-line box on an expanded time scale and the corresponding chromatograms.

As stated above, first column 14 includes a polar trifluoropropylmethyl polysiloxane stationary phase coating and, thus, first component 100, being the polar 1-pentanol, migrates more slowly therethrough. Similarly, second column 16 includes a non-polar dimenthyl polysiloxane coating and, thus, second component 102, being a non-polar n-octane, migrates more slowly therethrough. The result is that in the absence of a pressurized pulse, the band trajectory plots E and F for these components cross just prior to elution from column ensemble 14, 16. The peak apex separation, generally indicated at H', is less than 0.5 s, and only a single peak is observed in the chromatogram.

For the case illustrated in FIGS. 2(a) and (d), the pressurized pulse, $C_a$–$D_a$, is applied while both components 100 and 102, illustrated by band trajectories $E_a$ and $F_a$, are still on first column 14 (i.e. below horizontal line A). Since pressurized pulse $C_a$–$D_a$ results in an increase in pressure at column junction point 28, the pressure drop along first column 14 is reduced, and the local migration velocities of both components 100 and 102 are reduced. This effect is illustrated by the shallower slope of band trajectories $E_a$ and $F_a$. This results in greater residence time on first column 14 and the ensemble retention times being shifted to greater values. However, as seen in FIG. 2(d), peak-apex separation $H_a$ is not significantly changed relative to non-pulse peak-apex separation H'.

For the case illustrated in FIGS. 2(b) and (e), the pressurized pulse, $C_b$–$D_b$, is applied after first component 100 has crossed junction point line A, but before second component 102 has reached junction point line A. The larger pressure at column junction point 28 during pressurized pulse $C_b$–$D_b$ results in an increase in local carrier gas velocity on second column 16 (above junction point line A) and, thus, first component 100 accelerates as illustrated by the steeper slope of band trajectory $E_b$. The result is a decrease in ensemble retention time for first component 100. On the other hand, because second component 102 is still on first column 14 (below junction point line A) when pressurized pulse $C_b$–$D_b$ is applied, its migration rate decreases appreciably during pressurized pulse $C_b$–$D_b$. Therefore, band trajectory $F_b$ arrives at junction point line A considerably later than without pressurized pulse $C_a$–$D_a$ (see band trajectory F'). This results in an increase in ensemble retention time. The overall result in this scenario, as seen in FIG. 2(e), is a differential shift in individual retention times for first component 100 and second component 102 as illustrated by peak-apex separation $H_b$.

For the case illustrated in FIGS. 2(c) and (f), the pressurized pulse, $C_c$–$D_c$, is applied after both components 100 and 102 have migrated across junction point line A into second column 16. Since pressurized pulse $C_c$–$D_c$ results in an increase in pressure at column junction point 28, the pressure drop along second column 16 is increased, and the local migration velocities of both components 100 and 102 are sharply increased. This effect is illustrated by the steeper slope of band trajectories $E_c$ and $F_c$. This results in reduced residence time on second column 16 and the ensemble retention times being shifted to smaller values. However, as seen in FIG. 2(f), peak-apex separation $H_c$ is not significantly changed relative to non-pulse peak-apex separation H'.

These results illustrated in FIGS. 2(a)–(f) illustrate that ensemble values of peak-apex separation can be significantly increased for components that are on opposite sides of junction point line A when the pressurized pulse C–D is applied. For components that are on the same side of junction point line A during the pressurized pulse C–D, significant retention time shifts occur, but peak-apex separations and thus the pattern of peaks eluting from column ensemble 14, 16 are not significantly changed.

Figure 5:
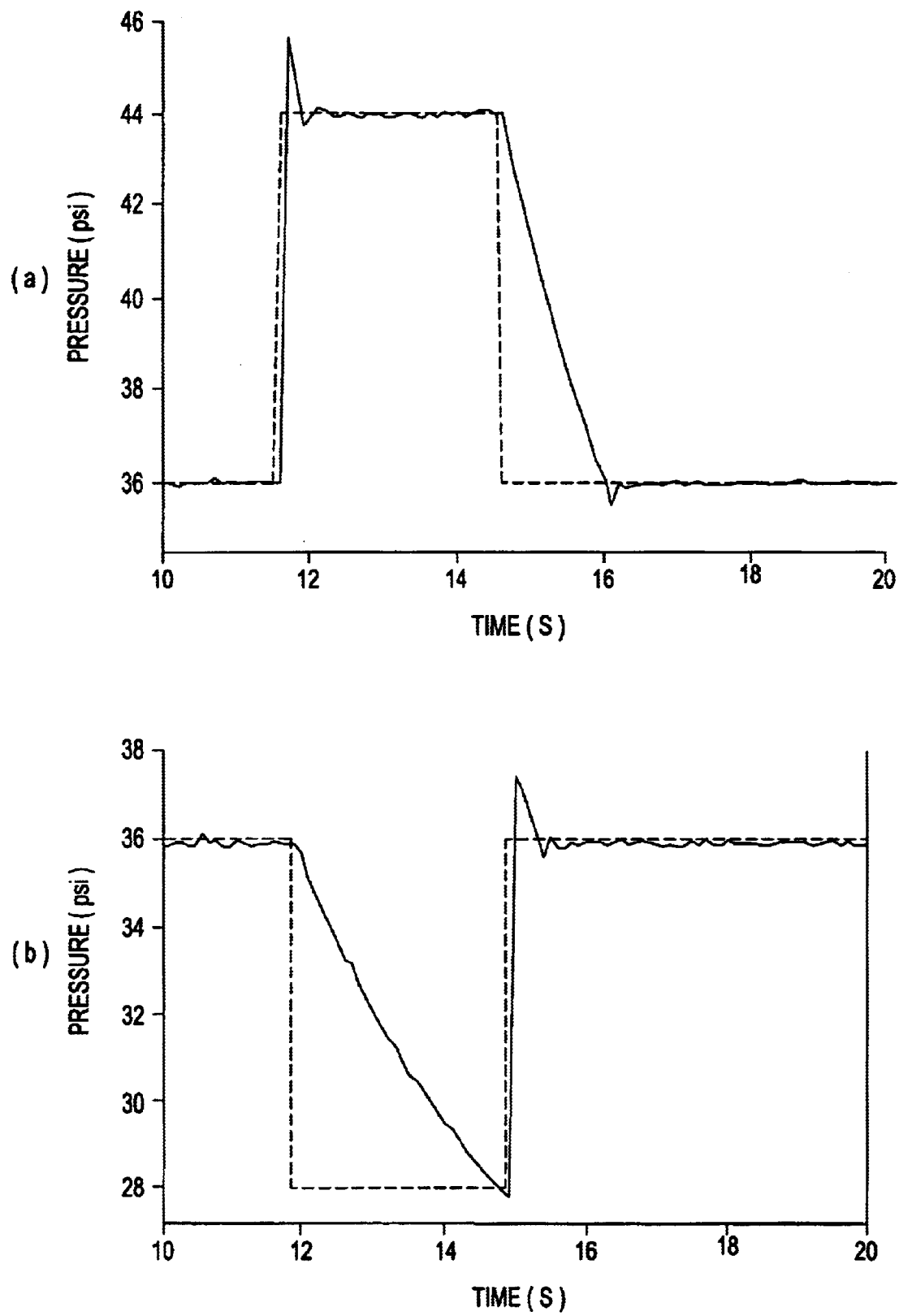
FIG. 5*a* illustrates an upward pressurized pulse applied to a column junction point, wherein the dashed line illustrates a nominal pulse shape.
FIG. 5*b* illustrates a downward pressurized pulse applied to the column junction point, wherein the dashed line illustrates a nominal pulse shape.

Referring now to FIGS. 3(a)–(e) and 4(a)–(f), chromatograms obtained with upward and downward pressurized pulses, respectively, initiated at various times after the sample injection are illustrated. Each of the figures is recorded at various pulse-initiation-time-after-injection times. For reference in each of these figures, the peak-apex retention time for a single peak containing both first component 100 and second component 102 is approximately 29.5 s, without using a pressurized pulse, as indicated by vertical line Z. As seen in FIGS. 5(a) and (b), the actual pulse shapes are illustrated as an upward pressurized pulse and a downward pressurized pulse, respectively. It may be important to note that an upward pulse (to higher pressure at column junction point 28) results in lower carrier gas velocity on first column 14 and higher velocity on second column 16. The opposite situation occurs for a downward pressurized pulse.

Figure 3:
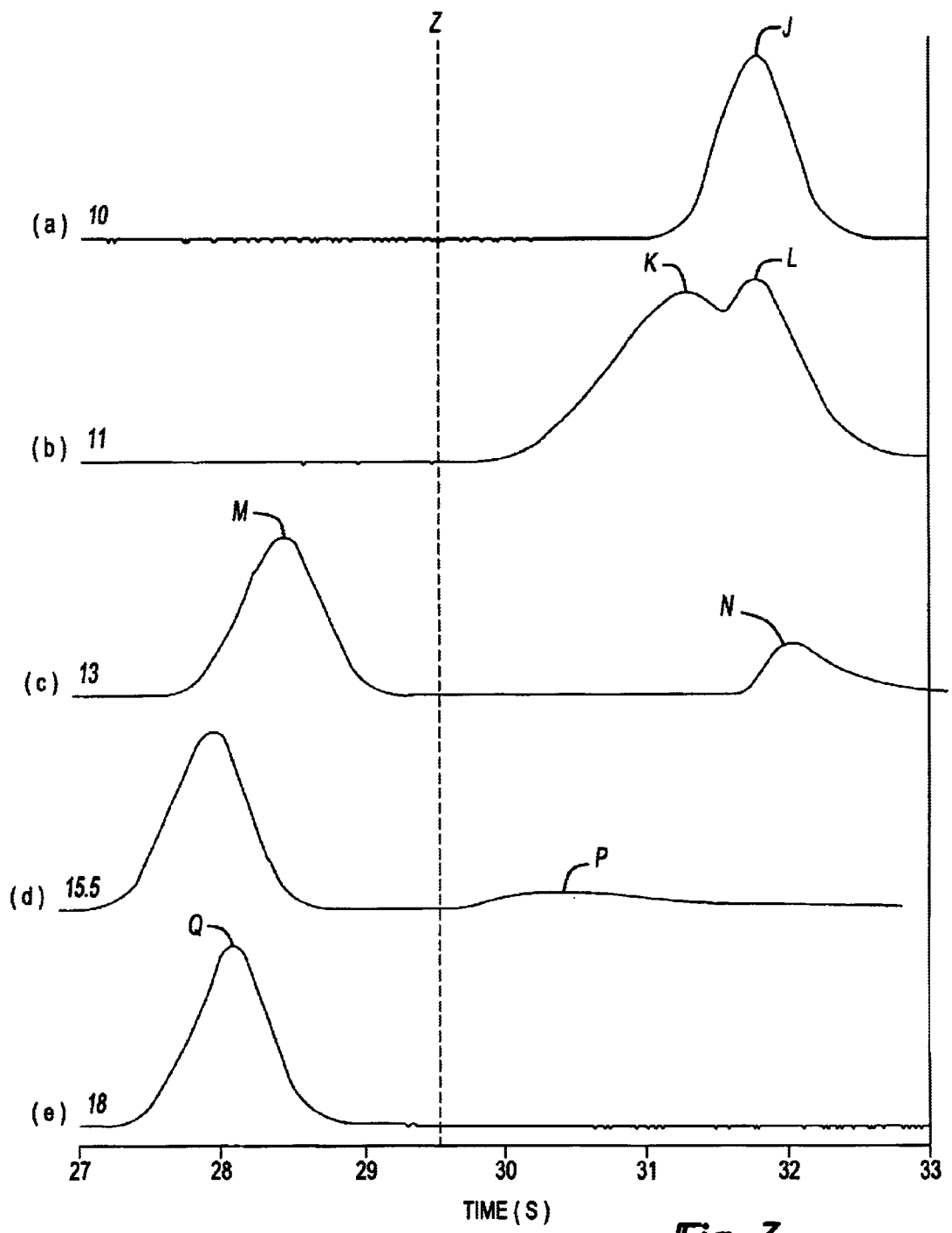
FIGS. 3(*a*)–(*e*) is a series of chromatograms illustrating the result of application of an upward pressurized pulse applied at 10 s, 11 s, 13 s, 15.5 s, and 18 s, respectively, after injection.
Figure 4:
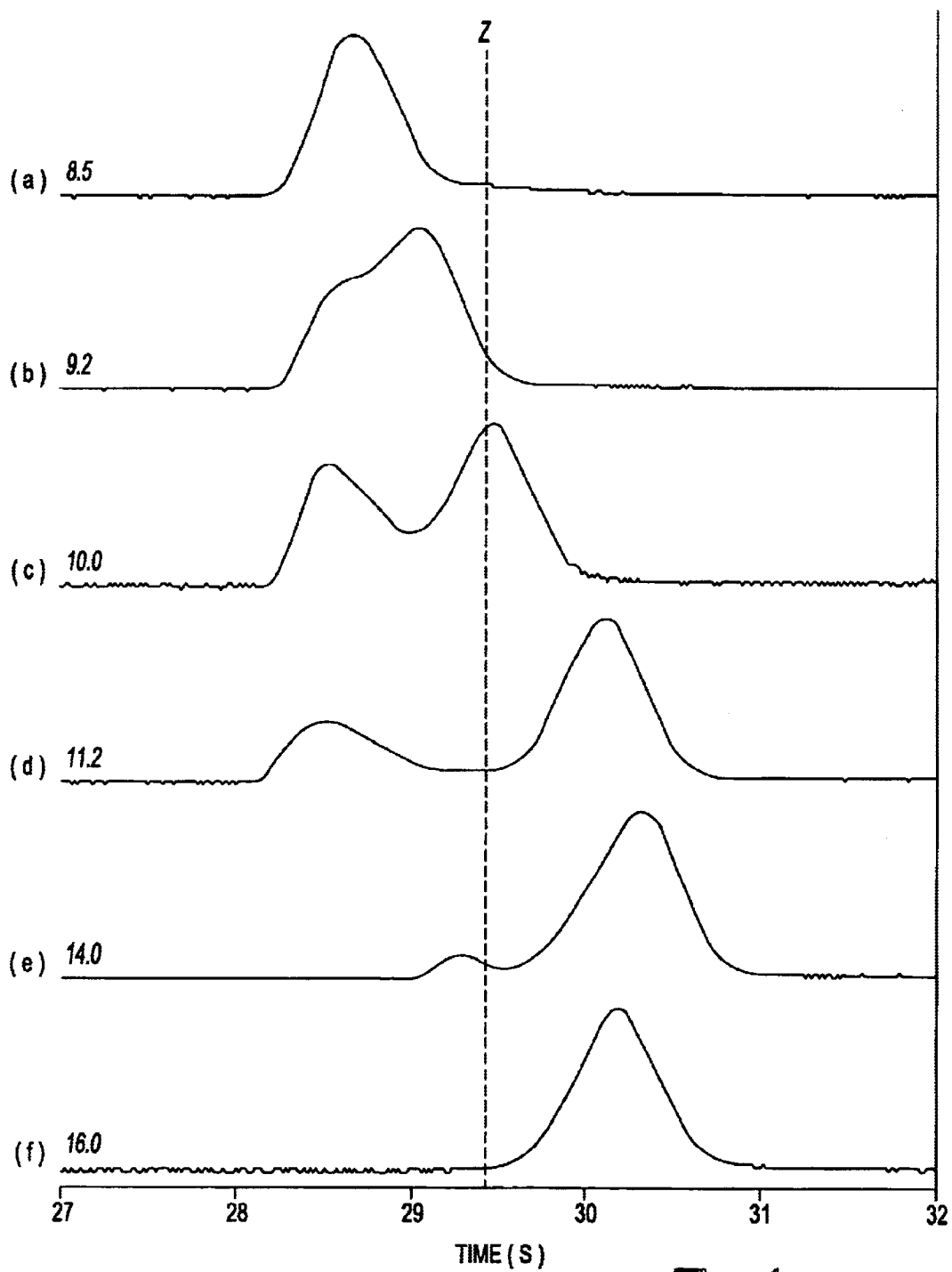
FIGS. 4(*a*)–(*f*) is a series of chromatograms illustrating the result of application of a downward pressurized pulse applied at 8.5 s, 9.2 s, 10.0 s, 11.2 s, 14.0 s, 16.0 s, respectively, after injection.

Referring in particular to FIG. 3(a), a pulse initiation time of 10.0 seconds after analyte mixture injection results in the entire pulse J occurring while both components 100 and 102 are on first column 14. This shifts the apex of peak J to a retention time of approximately 31.8 s, but has very little change in the shape of the peak. Referring to FIG. 3(b), when the pressurized pulse initiation time is delayed until 11.0 seconds after injection, both components 100 and 102 are on first column 14 at the beginning of the pressurized pulse, but part of first component 100 crosses column junction point 28 before the end of the pressurized pulse. This results is a broad, distorted double peak K and L.

As seen in FIG. 3(c), with a pulse initiation time of 13.0 s, first component 100 has completely crossed column junction point 28 prior to the pressurized pulse and second component 102 remains on first column 14 during the entire duration of the pressurized pulse. This results in a large shift of peak M to lower ensemble retention time for first component 100 and no significant change in retention time for second component 102, illustrated by peak N, relative to the 10.0-s pulse initiation time. The peak-apex separation for the 13.0-s delay case is 3.8 seconds. The peak tailing observed for second component 102 in FIG. 3(c) is often seen for alcohols and is observed even when only this example compound is injected and no pressurized pulse is used.

Referring now to FIG. 3(d), with a 15.5-s pulse initiation time, second component 102 reaches column junction point 28 before the pressurized pulse is complete. Consequently, a very broad, low-amplitude feature P is observed in the chromatogram. As seen in FIG. 3(e), with an 18.0-s pulse initiation time, both components have migrated across column junction point 28 prior to pulse initiation and only a single peak Q is seen in the chromatogram. However, the peak apex retention time has shifted by 1.5 seconds relative to the case with no pressurized pulse.

The same general trends are observed for the downward pressurized pulse illustrated in FIGS. 4(a)–(f), but the retention-time shifts relative to the no-pressure-pulse case (broken vertical line Z) are in the opposite direction. In addition, the maximum peak separation is only 1.8 s, compared to 3.8 seconds for the upward pressurized pulse case above. For the no-pressurized-pulse case, the elution times for first column 14 for components 100 and 102 differ by about 4.9 seconds.

Figure 6:
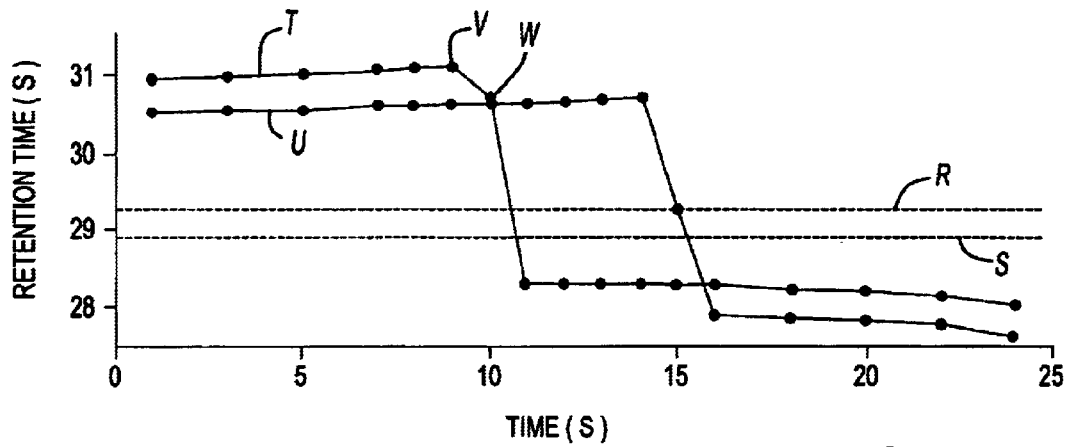
FIG. 6 is a graph illustrating the relationship between ensemble retention-time vs. pulse initiation-time for the pair of illustrative components for an upward pressurized pulse.

FIG. 6 illustrates a graph of ensemble retention-time vs. pulse initiation-time for first component 100 and second component 102 for an upward pressurized pulse with a 3.0 seconds nominal pulse width. A pair of broken horizontal lines R and S illustrate the calculated ensemble retention times for the case of no pressurized pulse for first component 100 and second component 102, respectively. Line T represents first component 100, while line U represents second component 102.

For an upward pressurized pulse, pulse initiation times less than 9 seconds result generally in a constant shift in retention times of about 1.6 seconds for both components since the pressurized pulse is complete before either component reaches column junction point 28. This is illustrated by the relative shift of lines R and T and lines S and U. For pulse initiation times in the range of about 9–11 s, first component 100 reaches column junction point 28 before completion of the pressurized pulse, and the retention time for first component 100 sharply decreases at Point V. For pulse initiation times in the range of about 11–14 s, the entire pressurized pulse occurs while first component 100 is on second column 16 and second component 102 is on first column 14. Here, a separation of 2.3–2.4 seconds is observed with the higher values occurring near the end of this time interval because of carrier gas acceleration. If the pressurized pulse initiation time is in the range of about 16–24 s, both components 100 and 102 are on second column 16 during the entire pressurized pulse and the resultant peaks illustrate nearly equal shifts to shorter retention times. As the pressurized pulse initiation time is further increased, one or both peaks elute from column ensemble 14, 16 before the pressurized pulse is completed and the retention times return to their no-pulse values.

It may be important to note that in FIG. 6, lines T and U cross for a pulse initiation time of about 10 seconds. This is explained by reference to the band migration trajectory plots in FIGS. 2(a)–(f). Without a pressurized pulse, the band trajectories E and F cross just prior to elution from column ensemble 14, 16 with the result that second component 102 elutes from column ensemble 14, 16 about 0.4 seconds before first component 100 as indicated by H'. With an upward pressurized pulse beginning 10 seconds after injection, first component 100 reaches column junction point 28 before the end of the pressurized pulse and its ensemble retention time is shifted lower by about 0.4 seconds. This results in complete co-elution of the two components at point W. Further delay in the start of the pressurized pulse by 1 second results in a larger shift for first component 100, resulting in an elution-order change and a relatively large separation.

Figure 7:
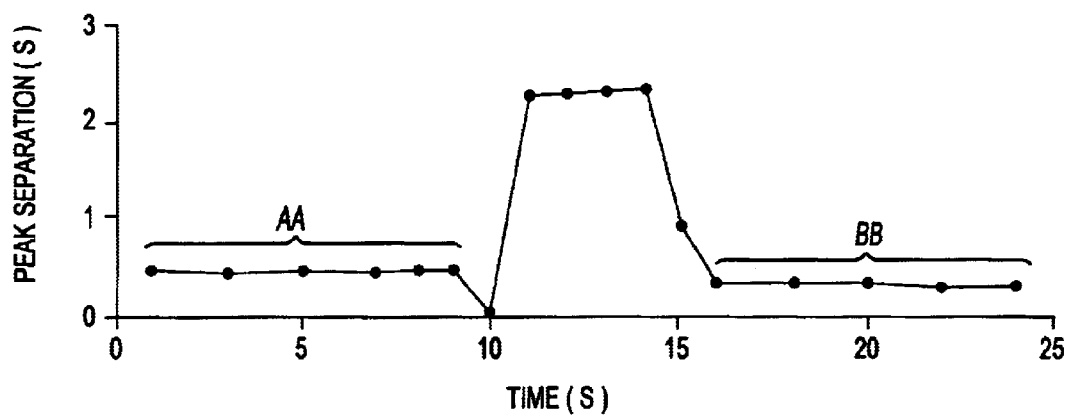
FIG. 7 is a graph illustrating the relationship between peak separations vs. pulse initiation-time for the pair of illustrative components for an upward pressurized pulse.

Similarly, FIG. 7 illustrates a graph of ensemble peak separation vs. pulse initiation-time for first component 100 and second component 102 for an upward pressurized pulse with a 3.0 seconds nominal pulse width. Peak separation with no pressurized pulse is about 0.4 seconds as shown by the separation of lines R and S in FIG. 6. The nearly flat regions, generally indicated at AA and BB, are expected from the retention time plots in FIG. 6. The maximum predicted peak separation for the upward pressurized pulse illustrated in FIG. 7 is about 2.4 s, while measured peak separations are about 3.8 seconds.

Figure 8:
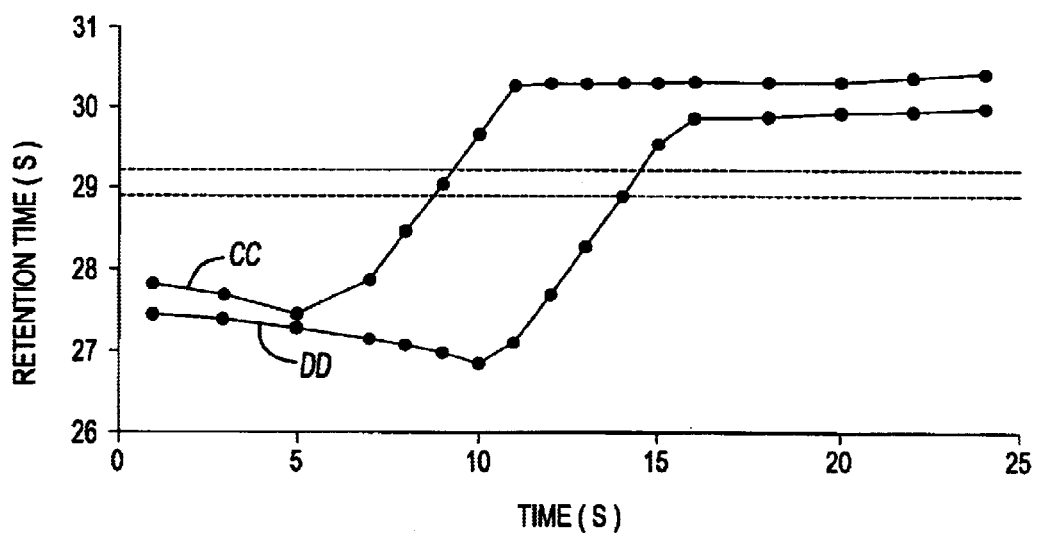
FIG. 8 is a graph illustrating the relationship between ensemble retention-time vs. pulse initiation-time for the pair of illustrative components for a downward pressurized pulse.

FIG. 8 is similar to FIG. 6 except the data is for the case of a downward pressurized pulse with a nominal width of 3.0 s, rather than an upward pressurized pulse. Line CC represents first component 100, while line DD represents second component 102. For the downward pressurized pulse with initiation times less than about 4 s, the entire pulse is complete before either components 100 or 102 reaches column junction point 28 and the retention times decrease only slightly in this interval with increasing delay in the pressurized pulse initiation. For pulse initiation times in the range of about 4–10 s, first component 100 reaches column junction point 28 prior to completion of the pressurized pulse. Consequently, its ensemble retention time increases with increasing initiation time due to the lower carrier gas velocity on second column 16 during the pressurized pulse. Second component 102 reaches column junction point 28 in about 10 s, and for pulse initiation times greater than about 10 s, the ensemble retention time for second component 102 increases rapidly with increasing pulse initiation time until about 16 seconds when second component 102 crosses column junction point 28. Further increases in pulse initiation time have only a minor effect on retention times until about 26 seconds when components 100 and 102 begin to elute from column ensemble 14, 16 before completion of the pressurized pulse. For pulse initiation times greater than about 30 s, both components elute prior to the start of the pressurized pulse and the retention times are the same as the no-pulse values.

As can be seen in FIG. 8, lines CC and DD do not cross as in the case illustrated in FIG. 6. In other words, a downward pressurized pulse causes the retention time for first component 100 to shift to larger values for pulse initiation times greater than five seconds. There is no change in elution order and thus lines CC and DD do not cross. It is interesting to note that the shift in ensemble retention times for first component 100 occurs for initiation times greater than 8 seconds for the upward pressurized pulse (see FIG. 6) and for times greater than 5 seconds for the downward pulse (see FIG. 8). This is the result of the lower carrier gas velocity on first column 14 during an upward pulse and the higher carrier gas velocity on first column 14 during a downward pulse.

Figure 9:
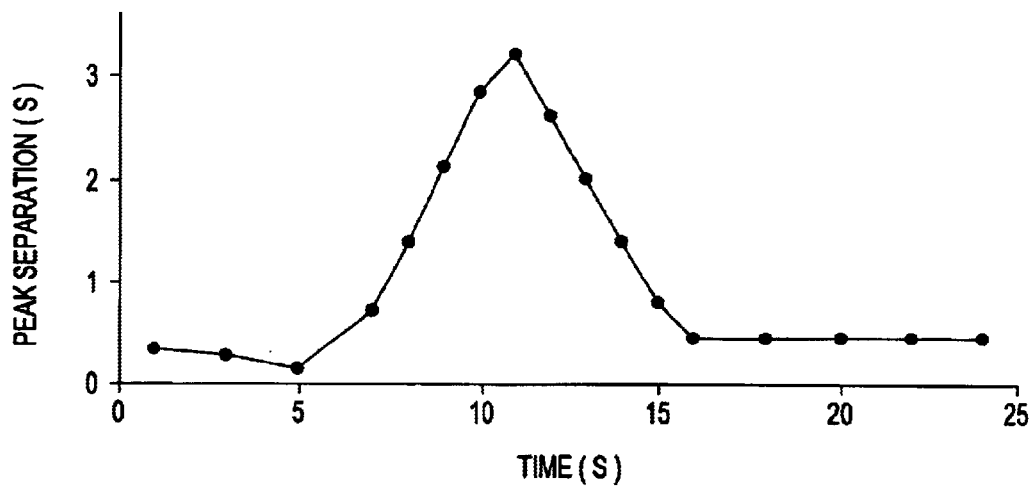
FIG. 9 is a graph illustrating the relationship between peak separations vs. pulse initiation-time for the pair of illustrative components for a downward pressurized pulse.

Referring now to FIG. 9, the triangularly shaped peak-separation vs. pulse-initiation-time plot for the downward pressurized pulse is the result of the increased carrier gas velocity on first column 14 during the pressurized pulse. This causes second component 102 to begin shifting to larger retention time values for pulse initiation times greater than 10 s; while component 100 has not completely shifted to higher values for initiation times less than 11 seconds. For the downward pressurized pulse, the maximum predicted peak separation as seen in FIG. 9 is about 3.3 s, while measured peak separations is about 1.7 seconds. These differences between the predicted and observed maximum peak separation values are due in part to the pressurized pulse shapes illustrated in FIGS. 4(a) and (b).

Figure 10:
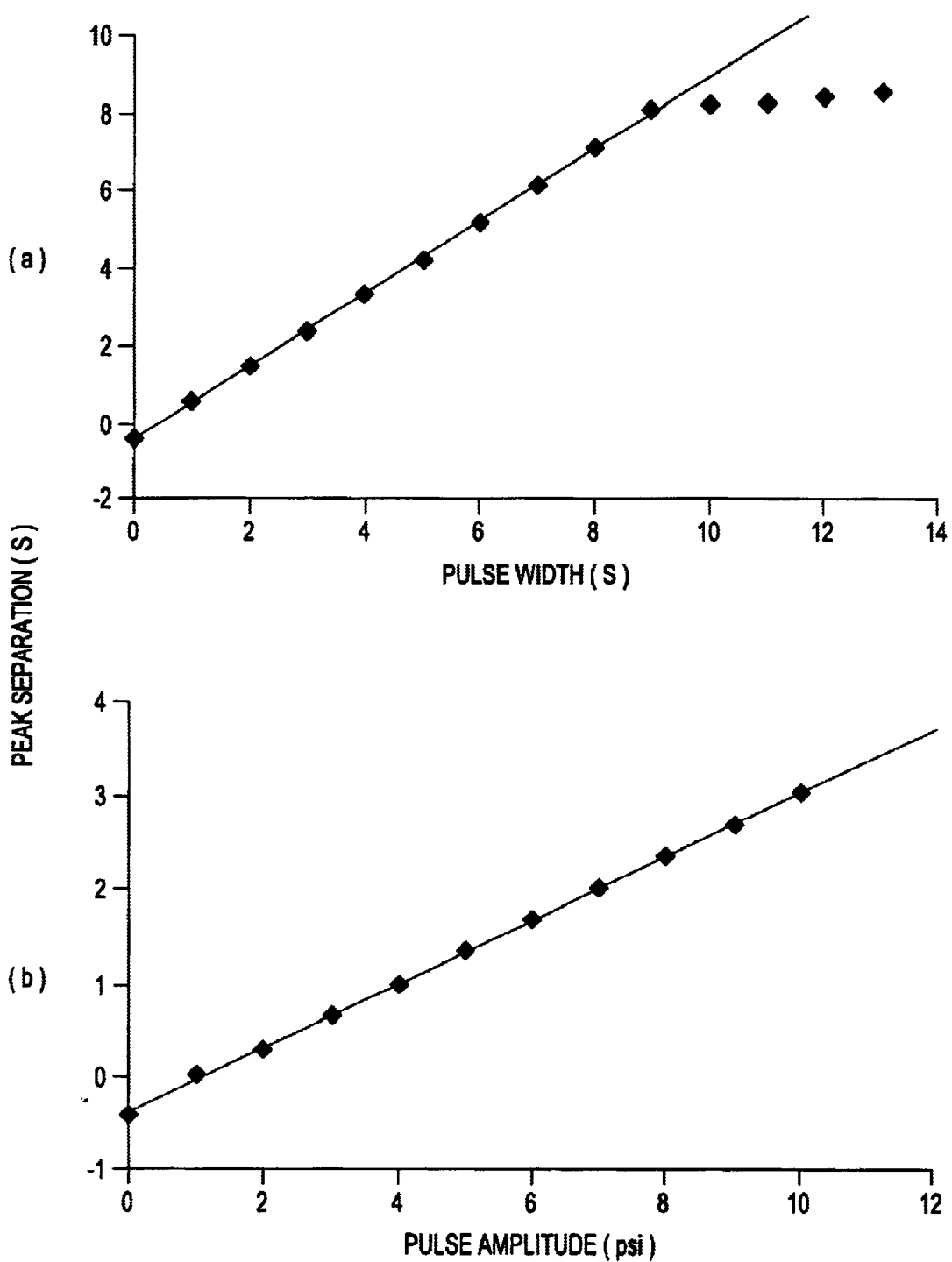
FIG. 10(a) is a graph illustrating the relationship between peak separation vs. pressurized pulse width for the pair of illustrative components.
FIG. 10(b) is a graph illustrating the relationship between peak separations vs. pressurized pulse amplitude for the pair of illustrative components.

FIGS. 10(a) and (b) illustrates the effect on peak separation caused by changes in the pressurized pulse width $\Delta t$ and amplitude $\Delta P$ for the case of an upward pressurized pulse, respectively. With particular reference to FIG. 10(a), $\Delta P$ is held constant at 8.0 psi. Similarly, with reference to FIG. 10(b), $\Delta t$ is held constant at 3.0 seconds. For both FIGS. 10(a) and (b), the pressurized pulse initiation time is 12 seconds such that first component 100 has crossed column junction point 28 but second component 102 is still on first column 14 at the start of the pressurized pulse.

Referring now to FIG. 10(a), for pulse widths up to about 9.0 s, the peak separation is nearly linear with varying pulse width. For pulse widths greater than 9.0 s, second component 102 crosses column junction point 28 prior to the end of the pressurized pulse and, thus, has little effect on peak separation.

Referring now to FIG. 10(b), it can be seen that peak separation vs. pulse amplitude remains generally linear for the amplitude range 2–10 psi. Therefore, because of the peak separation being proportional to the pressurized pulse amplitude and width, the peak separation should be proportional to the pressurized pulse area ($\Delta P \Delta t$).

According to the principles of the present invention, a gas chromatography system is provided that employs relatively narrow pressurized pulses to control the separation of specific or discrete pair of components eluting from a column ensemble 14, 16. For mixture components that are on the same column during the pressurized pulse, little change in peak pattern and peak-pair separation occurs in the ensemble chromatogram. However, relatively large peak separation increases are observed only when one of the pair of mixture components is on second column 16 and the other of the pair of mixture components is still on first column 14 during at least a portion of the pressurized pulse. The principles of the present invention are particularly useful for complex mixtures where most components are adequately separated, yet it is necessary to obtain enhanced separations for a relatively few component pairs or small groups without loosing separation quality for the rest of the mixture components. This approach also may be more useful than pressure (selectivity) tuning and programming since for most of the duration of the analysis the quiescent pressure at column junction point 28 can be adjusted to give minimum ensemble void time. It is important to note that instead of applying a set pressure at the column junction point, which would invariably cause other previously separated component pairs to now co-elute, the present invention applies a brief pressurized pulse at an optimal time to cause a targeted pair of components to elute separately without adversely effecting the remaining components in the mixture.

Furthermore, it has been shown that upward pressurized pulses may be more useful than downward pulses for several reasons. First, an upward pressurized pulse results in a decrease in the carrier gas velocity on first column 14, and this increases the available time for the pressurized pulse to be completed before the second component reaches the junction. Second, a downward pressurized pulse is more likely to result in sample loss through the vent line if the pressure during the pressurized pulse falls below the pressure that would exist at column junction point 28 in the absence of the pressure controller. Third, the pressure equilibration time is smaller for an upward pulse for any specified quiescent-pressure value. However, downward pressurized pulses do have some useful applications.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A gas chromatography method for separating components of an analyte mixture comprising:
   providing first and second chromatography columns for separating the components of the analyte mixture, said first chromatography column having an outlet coupled in series to an inlet of said second chromatography column to define a column junction point;
   injecting the analyte mixture into an inlet of said first chromatography column thereby causing at least partial elution separation of the analyte mixture at said column junction point;
   determining an optimal pulse initiation time between when a first of a discrete pair of components has entered said second chromatography column and the other of said discrete pair of components remains in said first chromatography column;
   applying a pressurized pulse of fluid at said column junction point at said optimal pulse initiation time to enhance elution separation of said discrete pair of components at said outlet of said second chromatography column;
   detecting elution separation of the analyte mixture at said outlet of said second chromatography column.

2. The gas chromatography method according to claim 1, further comprising detecting elution separation of the analyte mixture at said column junction point and outputting a signal.

3. The gas chromatography method according to claim 2 wherein said step of detecting elution separation of the analyte mixture at said column junction point and outputting a first signal is accomplished using a flame-ionization detector.

4. The gas chromatography method according to claim 2 wherein said step of detecting elution separation of the analyte mixture at said column junction point and outputting a first signal is accomplished using a thermal-conductivity detector.

5. The gas chromatography method according to claim 2 wherein said step of detecting elution separation of the analyte mixture at said column junction point and outputting a first signal is accomplished using a photo-ionization detector.

6. The gas chromatography method according to claim 2 wherein said step of determining an optimal pulse initiation time includes determining an optimal pulse initiation time in response to said signal.

7. The gas chromatography method according to claim 6 wherein said step of determining an optimal pulse initiation time in response to said signal, further comprises:
   determining a maximum value of said elution separation of said discrete pair in reference to varying pulse initiation times; and
   setting said optimal pulse initiation time to achieve said maximum value of said elution separation of said discrete pair of components.

8. The gas chromatography method according to claim 6 wherein said step of determining an optimal pulse initiation time in response to said signal, further comprises:
   determining an available time range when only one of said discrete pair of component passes said column junction point; and
   setting said optimal pulse initiation time within said available time range.

9. A gas chromatography method for separating components of an analyte mixture comprising:
   providing first and second chromatography columns for separating the components of the analyte mixture, said first chromatography column having an outlet coupled in series to an inlet of said second chromatography column to define a column junction point;
   injecting the analyte mixture into an inlet of said first chromatography column thereby causing at least partial elution separation of the analyte mixture at said column junction point;
   determining an optimal pulse initiation time;
   applying a pressurized pulse of fluid at said column junction point at said optimal pulse initiation time to enhance elution separation of said discrete pair of components at said outlet of said second chromatography column;
   detecting elution separation of the analyte mixture at said outlet of said second chromatography column,
   wherein said step of applying a pressurized pulse of fluid at said column junction point at said optimal pulse initiation time to enhance elution separation of a discrete pair of components at said outlet of said second chromatography column comprises:
      providing an electronic pressure controller in fluid communication with said column junction point;
      providing a pressurized fluid source coupled to said electronic pressure controller to supply said pressurized fluid to said electronic pressure controller;
      outputting a control signal to said electronic pressure controller at said optimal pulse initiation time from a central processing unit; and
      actuating said electronic pressure controller in response to said control signal, thereby applying said pressurized fluid to said column junction point at said optimal pulse initiation time.

10. A gas chromatography system for separating components of an analyte mixture, said gas chromatography system comprising;

an inlet system for providing a sample of the analyte mixture entrained on a stream of a carrier gas;

a first column fluidly coupled to said inlet system, said first column receiving said sample from said inlet system and causing at least partial separation of the components;

a second column fluidly coupled to said first column along a column junction point, said second column receiving said components eluting from said first column, said second column causing further separation of the components;

a ensemble detector operably coupled to said second column, said ensemble detector sensing said components eluting from said second column, said ensemble detector outputting a first signal;

a pressure controller operably coupled to said column junction point, said pressure controller applying a pressurized pulse in response to a control signal during a time when a first of a discrete pair of components has entered said second column and the other of said discrete pair of components remains in said first column; and a controller operably coupled to said pressure controller, said controller outputting said control signal in response to said first signal.

11. The gas chromatography system according to claim 10, further comprising:

a column junction point detector operably coupled to said column junction point, said column junction point detector sensing said components eluting from said first column, said column junction point detector outputting a second signal.

12. The gas chromatography system according to claim 11 wherein said controller comprises:

a central processing unit operably receiving said second signal and calculating an optimal pulse initiation time in response to said second signal, said central processing unit outputting said control signal to said pressure controller at said optimal pulse initiation time to enhance elution separation of a discrete pair of components of the analyte mixture.

13. The gas chromatography system according to claim 10, further comprising:

a pressurized fluid source operably coupled to said pressure controller, said pressurized fluid source supplying a pressurized fluid to said pressure controller so as to output said pressurized pulse.

14. The gas chromatography system according to claim 10, further comprising:

a venting system fluidly coupled to an output of said pressure controller to enable dissipation of said pressurized pulse.

15. The gas chromatography system according to claim 14 wherein said venting system further comprises:

a restrictor disposed between said pressure controller and an atmospheric vent, said restrictor limiting flow between said pressure controller and said atmospheric vent.

16. The gas chromatography system according to claim 10 wherein said column junction point detector is a flame-ionization detector.

17. The gas chromatography system according to claim 10 wherein said column junction point detector is a thermal-conductivity detector.

18. The gas chromatography system according to claim 10 wherein said column junction point detector is a photo-ionization detector.

* * * * *